(12) United States Patent
Gately et al.

(10) Patent No.: US 6,225,117 B1
(45) Date of Patent: May 1, 2001

(54) ANTIBODIES AGAINST HUMAN IL-12

(75) Inventors: Maurice Kent Gately, Parsippany; David Howard Presky, Glen Ridge, both of NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/232,522

(22) Filed: Jan. 19, 1999

Related U.S. Application Data

(60) Provisional application No. 60/072,333, filed on Jan. 23, 1998.

(51) Int. Cl.$^7$ .............................. C12N 5/16; C07K 16/00; C07K 16/24

(52) U.S. Cl. ....................... 435/332; 435/335; 435/343.2; 435/343.1; 530/388.23

(58) Field of Search .............................. 424/130.1, 139.1, 424/143.1, 144.1, 134.1; 435/343.1, 343.2, 332, 335; 530/388.2, 388.75, 388.23

(56) References Cited

U.S. PATENT DOCUMENTS

| | | |
|---|---|---|
| 5,780,597 | 7/1998 | Gately et al. . |
| 5,811,523 | 9/1998 | Trinchieri et al. . |
| 5,853,697 | * 12/1998 | Strober et al. . |
| 5,853,721 | * 12/1998 | Gately et al. . |

FOREIGN PATENT DOCUMENTS

WO 95/24918    9/1995    (WO) .

OTHER PUBLICATIONS

Carter, et al., Production and Characterization of Monoclonal Antibodies to Human Interleukin–12, Hybridoma, vol. 16, No. 4, (1997).
Zou, et al., Structure–Function Analysis of the p35 Subunit of Mouse Interlukin 12, T Journal of Biological Chemistry, vol. 270, No. 11, pp. 5864–5871 (1995).
Gubler, et al., Coexpression Of Two Distinct Genes Is Required To Generate Secreted Bioactive Cytotoxic Lymphocyte Maturation Factor, Proc. Natl. Acad. Sci., vol. 88, pp. 4143–4147 (1991).
Wolf, et al., Cloning Of cDNA For Natural Killer Cell Stimulatory Factor, A Heterodimeric Cytokine With Multiple Biologic Effects On T And Natural Killer Cells, The Journal of Immunology, vol. 146, pp. 3074–3081 (1991).
Podlaski, et al., Molecular Characterization Of Interleukin 12, Archives Of Biochemistry And Biophysics, vol. 294, No. 1, pp. 230–237 (1992).
D–Andrea, et al., Production Of Natural Killer Cell Stimulatory Factor (Interleukin 12) By Peripheral Blood Mononuclear Cells, J. Exp. Med, vol. 176, pp 1387–1398 (1992).
Ling, et al., Human IL–12 p40 Homodimer Binds To The IL–12 Receptor But Does Not Mediate Biologic Activity, The Journal of Immunology, vol. 154, pp. 116–127 (1995).
Gillessen, et al., Mouse Interleukin–12 (IL–12) p40 Homodimer: A Potent IL–12 Antagonist, Eur. J. Immunol., vol. 25, pp. 200–206 (1995).
Chizzonite, et al., High and Low Affinity Receptors For Interleukin–12 (IL–12) On Human T–cells: Evidence For A Two Subunit Receptor By IL–12 And Anti–Receptor Antibody Binding, $2^{nd}$ International Cytokine Conference, Banff, Alberta, Oct. 1–5, 1994, vol. 6:A82a (Abstract) (1994).
Gately, et al., Measurement Of Human And Mouse Interleukin 12, Current Protocols In Immunology, vol. 1, J.E. Coligan, et al. eds., John Wiley & Sons, pp. 6.16.1–6.16.8 (1995).
Mattner, et al., Genetically Resistant Mice Lacking Interleukin–12 Are Susceptible To Infection With Leishmania Major And Mount A Polarized Th2 Cell Response, Eur. J. Immunol, vol. 26, pp. 1553–1559 (1996).
Magram, et al, IL–12–Deficient Mice are Defective in IFNγ Production and Type 1 Cytokine Responses, Immunity, vol. 4, pp. 471–481 (1996).
Chizzonite, et al., IL–12: Monoclonal Antibodies Specific For The 40–kDa Subunit Block Receptor Binding And Biologic Activity On Activated Human Lymphoblasts, The Journal Of Immunology, vol. 147, No. 5, pp. 1548–1556 (1991).
Stern, et al., Increasing The Antigen Binding Capacity Of Immobolized Antibodies, Techniques In Protein Chemistry IV, pp. 353–360 (1993).
Zhang, et al., Interleukin 12 At The Site Of Disease In Tuberculosis, J. Clin. Invest., vol. 93, pp. 1733–1739 (1994).
Sieling, et al., IL–12 Regulates T Helper Type 1 Cytokine Responses In Human Infectious Diseases, The Journal of Immunology, vol. 153, pp. 3639–3647 (1994).
Presky, et al., Evidence for Multiple Sites of Interaction between IL–12 and Its Receptor, Annals of the New York Academy of Science, vol. 795, pp. 390–393 (1996).
Cytokine Bulletin; Spring 1996, Genzyme, pp. 1–13.*

* cited by examiner

*Primary Examiner*—Christina Y. Chan
*Assistant Examiner*—Marianne DiBrino
(74) *Attorney, Agent, or Firm*—George W. Johnston; Patricia S. Rocha-Tramaloni; Robert A. Silverman

(57) ABSTRACT

The present invention relates to novel p75 heterodimer specific anti-human IL-12 antibodies that are characterized by a higher potency and greater efficacy in neutralizing human IL-12 bioactivity than known heterodimer specific IL-12 monoclonal antibodies. The heterodimer specific antibodies recognize one or more epitopes of the human IL-12 p75 heterodimer, but do not bind to the p40 subunit alone. The heterodimer specific IL-12 antibodies neutralize rhesus monkey IL-12 bioactivity with a potency similar to their potency for neutralizing human IL-12 bioactivity making them useful IL-12 antagonists for in vivo studies in the rhesus monkey.

23 Claims, 7 Drawing Sheets

16G2 HEAVY CHAIN VARIABLE REGION

```
                           27                                        54
CTG GAG GAG TCA GGA CCT AGC CTC GTG AAA CCT TCT CAG ACT CTG TCC CTC ACC
GAC CTC CTC AGT CCT GGA TCG GAG CAC TT  GGA AGA GTC TGA GAC AGG GAG TGG
Leu Glu Glu Ser Gly Pro Ser Leu Val Lys Pro Ser Gln Thr Leu Ser Leu Thr 81                                       108
TGT TCT GTC ACT GGC GAC TCC ATC ACC AGT GGT TAC TGG AAC TGG ATC CGG AAA
ACA AGA CAG TGA CCG CTG AGG TAG TGG TCA CCA ATG ACC TTG ACC TAG GCC TT
Cys Ser Val Thr Gly Asp Ser Ile Thr Ser Gly Tyr Trp Asn Trp Ile Arg Lys 135                                       162
TTC CCA GG  AAT AAA TT  GAG TAC ATG GGA TTC ATA AGT TAT AGT GGT AGC ACT
AAG GGT CCC TTA TT  AAA CTC ATG TAC CCT AAG TAT TCA ATA TCA CCA TCG TGA
Ph  Pro Gly Asn Lys Ph  Glu Tyr MET Gly Phe Ile Ser Tyr Ser Gly Ser Thr 189                                       216
TAC AAT ATT CCA TCT CTC AAA AAT CGA GTC TCC ATC ACT CGA GAC ACA TCC AAT
ATG TTA TTA GGT AGA GAG TT  TTA GCT CAG AGG TAG TGA GCT CTG TGT AGG TTA
Tyr Asn Asn Pro Ser Leu Lys Asn Arg Val Ser Ile Thr Arg Asp TTh Ser Asn 243                                       270
AAC CAG TAC TAC CTG CAG TTG AGT TCT GTG ACT ACT GAG GAC TCA GCC ACA TAT
TTG GTC ATG ATG GAC GTC AAC TCA AGA CAC TGA TGA CTC CTG AGT CGG TGT ATA
Asn Gln Tyr Tyr Leu Gln Leu Ser Ser Val Thr Thr Glu Asp Ser Ala Thr Tyr

297
TAC TGT GCA AGA TCT TCG GAT GCT TTG GAC TAC TGG GGC CGA GG  ACC ACG
ATG ACA CGT TCT AGA AGC CTA CGA AAC CTG ATG ACC CCG CGT CCC  TGG TGC
Tyr Cys Ala Arg Ser Ser Asp Ala Leu Asp Tyr Trp Gly Ala Gly Thr Thr
```

*FIG. 6*

20E11 HEAVY CHAIN VARIABLE REGION

```
                              27                                           54
GAG GAG TCA GGA CCT AGC CTC GTG AAA  CCT TCT CAG ACT CTG TCC CTC ACC TGT
CTC CTC AGT CCT GGA TCG GAG CAC T T  GGA AGA GTC TGA GAC AGG GAG TGG ACA
Glu Glu Ser Gly Pro Ser Leu Val Lys Pro Ser Gln Thr Leu Ser Leu Thr Cys 81                                          108
TCT GTC ACT GGC GAC TCC ATC ACC AGT  GGT TAC TGG AAC TGG ATC CGG AAA TTC
AGA CAG TGA CCG CTG AGG TAG TGG TCA  CCA ATG ACC TTG ACC TAG GCC T T  AAG
Ser Val Thr Gly Asp Ser Ile Thr Ser Gly Tyr Trp Asn Trp Ile Arg Lys Phe
                                        ‾‾‾ ‾‾‾ ‾‾‾ ‾‾‾

135                                          162
CCA GAT AAT ACA CTT GAG TAC ATG GGA TAC ATA  AGT TAC AGT GGT AGT ACT TAC
GGT CTA TTA TGT GAA CTC ATG TAC CCT ATG TAT  TCA ATG TCA CCA TCA TGA ATG
Pro Asp Asn Thr Leu Glu Tyr MET Gly Tyr Ile Ser Tyr Ser Gly Ser Thr Tyr
                                    ‾‾‾ ‾‾‾ ‾‾‾ ‾‾‾ ‾‾‾ ‾‾‾ ‾‾‾ ‾‾‾

189                                          216
TAC AAT CCA TCT CTC AGA AGT CGA ATC  TCC ATC ACT CGA GAC ACA TCC AAG AAC
ATG TTA GGT AGA GAG TCT TCA GCT TAG  AGG TAG TGA GCT CTG TGT AGG TTC TTG
Tyr Asn Pro Ser Leu Arg Ser Arg Ile Ser Ile Thr Arg Asp Thr Ser Lys Asn
‾‾‾ ‾‾‾ ‾‾‾ ‾‾‾ ‾‾‾ ‾‾‾ ‾‾‾

243                                          270
CGA TAC TCC ATG CAG TTG AAT TCT GTG ACT ACT  GAG GAC ACA GCC ACA TAT TAC
GTC ATG AGG TAC GTC AAC TTA AGA CAC TGA TGA  CTC CTG TGT CGG TGT ATA ATG
Gln Tyr Ser MET Gln Leu Asn Ser Val Thr Thr Glu Asp Thr Ala Thr Tyr Tyr

297
TGT GCA AGA TCC TCG GAT GCT ATG GAC TAC TGG GGC GC
ACA CGT TCT AGG AGC CTA CGA TAC CTG ATG ACC CCG CG
Cys Ala Arg Ser Ser Asp Ala MET Asp Tyr Trp Gly
            ‾‾‾ ‾‾‾ ‾‾‾ ‾‾‾ ‾‾‾ ‾‾‾
```

FIG. 7

ANTIBODIES AGAINST HUMAN IL-12

This application claims priority under 35 U.S.C. § 119(e) of provisional application Serial No. 60/072,333, filed Jan. 23, 1998.

FIELD OF THE INVENTION

This invention relates generally to IL-12 antibodies, and more specifically to anti-human IL-12 polyclonal and monoclonal antibodies.

BACKGROUND OF THE INVENTION

Interleukin-12 (IL-12), formerly known as cytotoxic lymphocyte maturation factor or natural killer cell stimulatory factor, is a 75-kDa (p75) heterodimeric cytokine composed of disulfide bonded 40-kDa (p40) and 35-kDa (p35) subunits. The p40 and p35 subunits are polypeptides which contain 306 amino acid residues and 197 amino acid residues, respectively (Gubler U., et al., Proc. Natl. Acad. Sci. USA, Vol. 88, 4143–4147 (1991)).

The p75 heterodimer is the biologically active form of IL-12 (Gubler, U., et al., 1991, Proc. Natl. Acad. Sci. USA, 88: 4143; Wolf, S. F., et al., 1991, J. Immunol., 146: 3074). The IL-12 p75 heterodimer both activates and boosts cell mediated immune responses against foreign antigens by stimulating production of Th1 helper cells, stimulating activated T and natural killer (NK) cells, enhancing lytic activity of NK/LAK cells, and stimulating production of IFN-γ by resting and activated T and NK cells.

The p40 subunit of IL-12 has been shown to be produced in excess of the p35 subunit and is found in both monomeric and dimeric forms (Podlaski, F. J., et al., 1992, Arch. Biochem. Biophys. 294: 230; D'Andrea, A., et al., 1992, J. Exp. Med., 176: 1387). IL-12 p40 homodimer is a potent IL-12 antagonist (Ling, P., et al., 1995, J. Immunol., 154: 116; Gillessen, S., et al., 1995, Eur. J. Immunol., 25: 200). In contrast to the p40 subunit, the p35 subunit of IL-12 has no known biological activity, and the p35 protein has only been found in association with the p40 subunit as part of the IL-12 p75 heterodimer. Therefore, there are two important types of epitopes presented by human IL-12: (1) epitopes presented by the p40 subunit; and (2) epitopes presented by the three dimensional conformation of the IL-12 p75 heterodimer. Consequently, we designate antibodies that recognize epitopes present on the IL-12 p75 heterodimeric protein but do not recognize epitopes present on the IL-12 p40 subunit protein "heterodimer specific" antibodies.

It has been found that known IL-12 antibodies are not optimally effective in substantially neutralizing IL-12 bioactivity. IL-12 antibodies which immunologically react with the p40 subunit do not optimally block the bioactivity of human IL-12. For example, use of antibodies which react with epitopes presented by the p40 subunit is particularly problematic because production of IL-12 p75 heterodimer has been shown to result in excess inactive p40 subunits relative to bioactive p75 heterodimer (Podlaski, F. J., 1992, Arch. Biochem. 294: 230; D'Andrea, A., et al., 1992, J. Exp. Med., 176: 1387). As a result, the p40 antibodies are not as effective as heterodimer specific antibodies in reducing detrimental effects of IL-12 because the p40 subunit alone is not bioactive, and p40 antibodies tend to bind to the inactive p40 subunits rather than those p40 subunits that are part of a bioactive p75 heterodimer.

Even known antibodies which react only with the p75 heterodimer, do not effectively neutralize IL-12 bioactivity. For example, a previously identified IL-12 p75 heterodimer specific antibody, called 20C2 (Chizzonite et al., Cytokine, 6: A82a (1994) and D'Andrea et al., J. Exp. Med., Vol. 176, 1387– 1398 (1992)), cannot substantially block human IL-12 stimulated PHA-activated lymphoblast proliferation and IFN-γ production.

Heterodimer specific antibodies which more effectively neutralize IL-12 bioactivity are needed to reduce detrimental effects of IL-12. Increased levels of IL-12 in serum or tissue are known to be involved in the development and progression of autoimmune disorders. Thus, IL-12 antibodies are useful antagonists for controlling diseases with pathologies that are mediated through immune mechanisms, particularly, diseases associated with aberrant Th1-type helper cell activity. Examples of such autoimmune disorders include multiple sclerosis, inflammatory bowel disease (IBD) including Crohn's disease and ulcerative colitis, rheumatoid arthritis and autoimmune diabetes mellitus. Other disease conditions which have been shown to benefit from the administration of IL-12 antibodies include transplantation/graft-versus-host disease and septic shock.

In accordance with this invention, it has been found that IL-12 antibodies obtained from a mammal deficient in the gene encoding the p35 subunit and/or the gene encoding the p40 subunit substantially neutralize IL-12 bioactivity.

SUMMARY OF THE INVENTION

In accordance with this invention, for the first time, antibodies which substantially neutralize the bioactivity of human IL-12 are produced using the methods described herein. Unlike other IL-12 p75 heterodimer specific antibodies, the heterodimer specific antibodies of the present invention neutralize at least 90% of human IL-12 bioactivity. In addition, IL-12 p75 heterodimer specific antibodies of the present invention cross react with rhesus monkey IL-12.

The p75 heterodimer specific IL-12 antibodies described herein are effective therapeutic agents for use in blocking IL-12 bioactivity to treat conditions mediated by undesirable IL-12 stimulated immunological responses. The highly neutralizing heterodimer specific IL-12 antibodies described herein are particularly useful inhibitors of IL-12 stimulated PHA-activated human lymphoblast proliferation and IFN-γ production by PHA-activated human lymphoblasts.

BRIEF DESCRIPTION OF THE DRAWINGS

As shown in FIG. 2, monoclonal antibodies 20C2, 20E11 and 5F2 are unique immunoglobulins. Monoclonal antibodies 16G2 and 16F2 appear identical by isoelectric focusing, but both are different from 20C2, 20E11 and 5F2.

As shown in FIG. 3, IL-12 monoclonal antibodies, 16G2 (Δ), 16F2 (○), 20E11 (:) and 5F2 (s) inhibit 0.25 ng/ml human IL-12 stimulated PHA-activated lymphoblast proliferation by at least 90%. In contrast, as shown in FIG. 3, previously known 20C2 (+) antibody does not substantially inhibit IL-12 stimulated PHA-activated human lymphoblast proliferation.

As shown in FIG. 4, the antibodies of the present invention are potent inhibitors of rhesus monkey IL-12 stimulated PHA-activated lymphoblast proliferation, in contrast to the 20C2 (+) antibody which has a minimal inhibitory effect on rhesus monkey IL-12 stimulated lymphoblast proliferation.

As shown in FIG. 5, antibodies 16F2 (○), 16G2 (■), 20E11 (s) and 5F2 (●) inhibit 0.25 ng/ml human IL-12 stimulated IFN-γ production by at least 90%. The dashed horizontal line at the lower end of the plot represents background IFN-γ production in the absence of IL-12. In contrast, as shown in FIG. 5, the 20C2 (Q) monoclonal antibody is unable to inhibit 0.25 ng/ml IL-12 stimulated IFN-γ production by more then 65%.

FIG. 6 is a nucleotide sequence encoding a portion of the heavy chain variable region of the p75 heterodimer specific 16G2 antibody, and the amino acid sequence deduced from this nucleotide sequence (SEQ ID NO:1).

FIG. 7 is a nucleotide sequence encoding a portion of the heavy chain variable region of the p75 heterodimer specific 20E11 antibody, and the amino acid sequence deduced from this nucleotide sequence (SEQ ID NO:3).

DETAILED DESCRIPTION OF THE INVENTION

Figure 1:
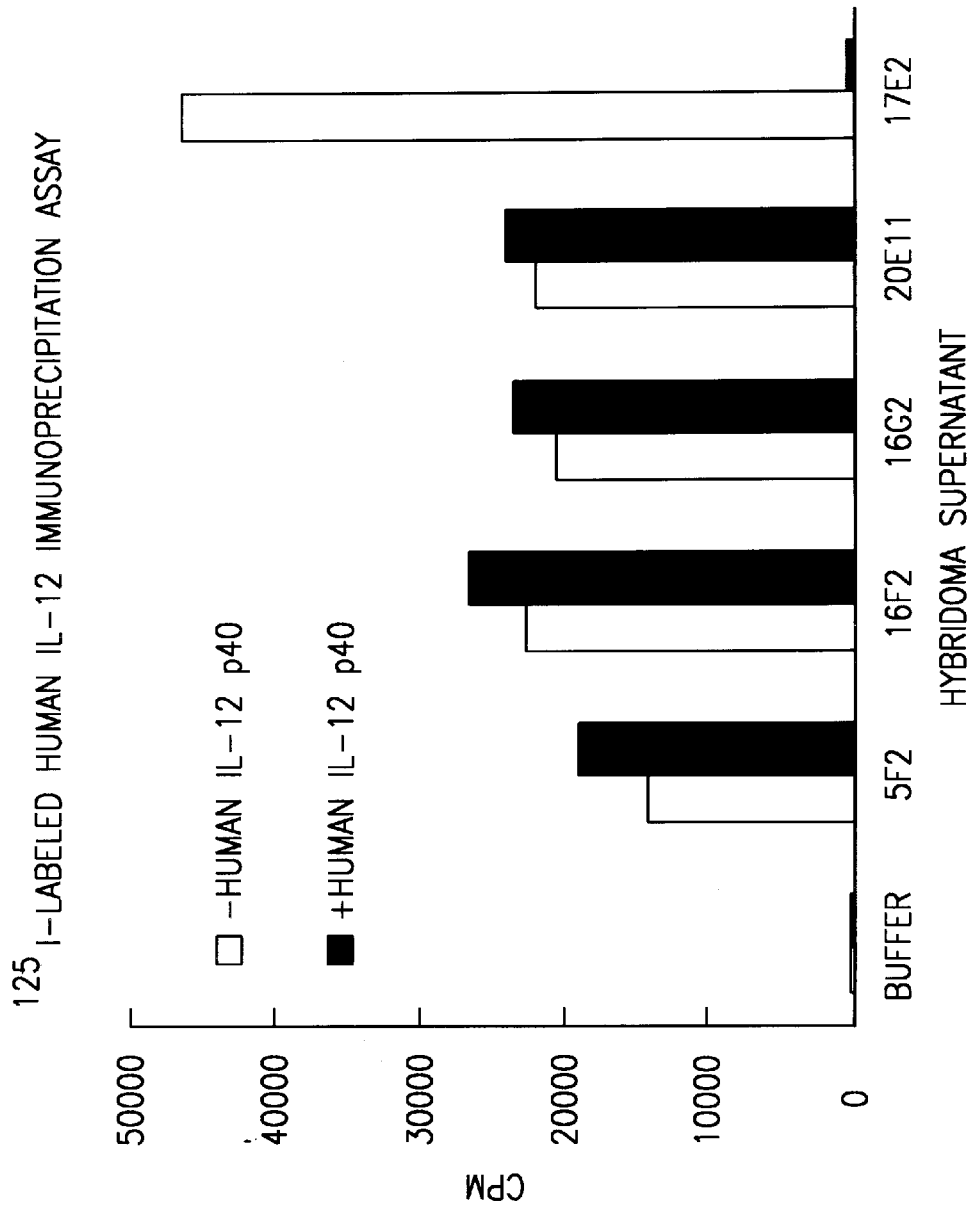
FIG. 1 is a graph showing capture of $^{125}$I-labeled human IL-12 by antibodies contained in supernatants from hybridomas HIL-12F3-5F2 (herein referred to as "5F2"), HIL-12F3-16F2 (herein referred to as "16F2"), HIL-12F3-16G2 (herein referred to as "16G2"), HIL-12F3-20E11 (herein referred to as "20E11"), and HIL-12F1-17E2 (herein referred to as "17E2") (open bars). The presence of unlabeled human IL-12 p40 subunit during the immunoprecipitation reaction (solid bars) did not block capture of $^{125}$I-labeled human IL-12 by monoclonal antibodies 5F2, 16F2, 16G2 and 20E11, demonstrating that these antibodies do not have high affinity for the IL-12 p40 subunit alone.

In accordance with the present invention, it has been found that when IL-12 antibodies are produced from mammals deficient in the gene encoding the p35 IL-12 subunit and/or the gene encoding the p40 IL-12 subunit, IL-12 antibodies are obtained which selectively immunologically react with epitopes of the p75 heterodimer of IL-12, and are identified by their ability to selectively immunologically react with the p75 heterodimer of human IL-12, but not immunologically react with the p40 subunit alone.

Unlike previously known IL-12 p75 antibodies, antibodies which substantially neutralize the bioactivity of human IL-12, i.e., neutralize at least about 90% bioactivity of human IL-12, are produced by the methods described herein. In addition, IL-12 p75 heterodimer specific antibodies of the present invention cross react with rhesus monkey IL-12.

The IL-12 antibodies described herein neutralize at least about 90% bioactivity of human IL-12 by inhibiting at least about 90% IL-12 induced PHA-activated human lymphoblast proliferation at concentrations of at least about 0.5 µg/ml, and/or inhibiting at least about 90% of IL-12 stimulated IFN-γ production by PHA-activated human lymphoblasts at concentrations of at least about 0.5 µg/ml. Furthermore, the antibodies described herein have been shown to specifically inhibit IL-12-induced, but not IL-2-induced, proliferation of PHA-activated human lymphoblasts. PHA-activated lymphoblasts are prepared as follows. Peripheral blood mononuclear cells (PBMC) were isolated (Gately et al., J. Natl. Cancer Inst., 69:1245 (1982)) and stimulated with 0.1% PHA-P (Difco Labs., Detroit, Mich.). After 3 days, the cultures were split 1:1 with fresh medium and recombinant 50 U/ml human IL-2 (provided by Dr. F. Khan, Hoffmann-La Roche Inc.) as described in Gately, M. K., Chizzonite, R. and Presky, D. H., Measurement of human and mouse interleukin 12, Current Protocols in Immunology, vol. 1. J. E. Coligan, A. M. Kruisbeek, D. H. Margulies, E. M. Shevach, and W. Strober, eds., John Wiley & Sons, Inc., New York, 1995, pp. 6.16.1–6.16.15. The PHA-activated lymphoblasts were used after an additional one day incubation period.

In accordance with the present invention, the IL-12 antibodies are identified for their ability to selectively bind the epitope presented by the p75 heterodimer, but not immunologically react with any epitope presented by the p40 subunit. This selectivity is defined by the fact that the IL-12 antibodies of this invention will react, at a certain minimal concentration, with an epitope solely presented by a given amount of the p75 heterodimer but will not react at that concentration with an epitope presented by the p40 subunit of that same given amount of this p75 heterodimer. In this way the antibodies of this invention have a higher affinity for an epitope solely presented by the p75 heterodimer than any epitope presented by the p40 subunit. Any conventional assay for identifying selective binding of the antibodies to the p75 heterodimer can be used. Generally, in such an assay, antibodies are incubated with human IL-12 p75 heterodimer to determine if the antibodies bind the p75 heterodimer. The antibodies are also incubated with human IL-12 p75 heterodimer in the presence and absence of the p40 subunit to determine if the presence of the p40 subunit blocks antibody binding or capture of the p75 heterodimer. For example, competitive immunoprecipitation assays (see Example 7 herein) can be used to demonstrate that the antibodies described herein selectively immunologically react with the p75 heterodimer of human IL-12, but are not immunologically reactive with the p40 subunit alone.

In accordance with the present invention, the IL-12 antibodies described herein are produced through the use of knock-out mammals. The knock-out mammals are deficient in the gene encoding the p35 subunit and/or the gene encoding the IL-12 p40 subunit and thus, do not express the IL-12 p75 heterodimer. When immunized with the IL-12 p75 heterodimer, the IL-12 p35 subunit deficient and/or the IL-12 p40 subunit deficient knock-out mammal recognizes the IL-12 p75 heterodimer as foreign and produces antibodies thereto. Preferably, the knock-out mammal is a mouse. In accordance with the present invention knock-out mammals are produced by methods that have been described in the art. Knock-out mammals can be produced by conventional means such as by mutation of the gene encoding the p35 IL-12 subunit and/or the p40 IL-12 subunit. For example, mice carrying a mutation in the IL-12 p35 subunit gene can be produced as described by Mattner, F., et al., Eur. J. Immunol., 26:1553–1559(1996). Mice carrying a mutation in the IL-12 p40 subunit gene can be produced as described by Magram, J., et al., Immunity, 4: 471–481 (1996).

In accordance with the present invention, polyclonal and monoclonal antibodies that selectively immunologically react with the P75 heterodimer of human IL-12 are produced from activated cells of the aforementioned knock-out mammal by any conventional means known in the art. Generally, the antibodies are produced by (a) immunizing a "knockout" mammal deficient in a gene encoding the p35 subunit and/or the p40 subunit with human p75 heterodimer to produce antibodies; (b) obtaining antibodies from the immunized mammal; and (c) screening the antibodies for their ability to selectively bind the epitope presented by the p75 heterodimer to obtain the selectively binding antibodies.

The IL-12 monoclonal antibodies of the present invention which selectively immunologically react with the human IL-12 p75 heterodimer are generally produced by a method including the following steps:

(1) immunizing a knock-out mammal, such as, for example, a mouse deficient in the gene encoding the IL-12 p35 subunit and/or IL-12 p40 subunit, with human IL-12 p75 heterodimer;

(2) selecting cells from the immunized knock-out mammal that have been activated to express antibodies against IL-12, such as, splenocytes or lymph node cells;

(3) fusing the harvested cells to myeloma cells to form hybridoma cells;

(4) selecting hybridoma cells which secrete antibodies that recognize human IL-12, for example, by testing hybridoma conditioned medium for the presence of anti-human IL-12 antibodies, for example, through the use of ELISA or immunoprecipitation assays employing labeled or unlabeled human IL-12; and (5) determining if the antibodies are p75 heterodimer specific by demonstrating that the antibodies immunologically react with an epitope of the p75 IL-12 heterodimer, but are not immunologically reactive with any epitope of the p40 subunit, by incubating the antibodies with human IL-12 p75 heterodimer to determine if the antibodies bind the p75 heterodimer, and then incubating the antibodies with human IL-12 p75 heterodimer in the presence and absence of the p40 subunit to determine if the presence of the p40 subunit blocks antibody binding or capture of the p75 heterodimer. For example, competitive immunoprecipitation assays (see Example 7 herein) can be used to demonstrate that the antibodies described herein selectively immunologically react with the p75 heterodimer of human IL-12, but are not immunologically reactive with the p40 subunit alone.

The method for producing the p75 heterodimer specific IL-12 monoclonal antibodies of the present invention can further comprise the step of determining the ability of the heterodimer specific IL-12 antibodies to inhibit both human and rhesus monkey IL-12 bioactivity in any in vitro or in vivo assay system for IL-12 bioactivity, such as assays for determining IL-12-stimulated proliferation of activated lymphocytes, IL-12-stimulated production of IFN-γ, or IL-12-stimulated enhancement of cytolytic activity.

The anti-human IL-12 antibodies of the present invention can be isolated to substantially pure form by standard methods known in the art, such as, for example, ammonium sulfate precipitation, affinity chromatography, or ion exchange chromatography.

Variations of the method for obtaining the antibodies of the present invention are also encompassed within the present invention. Methods known in the art such as, for example, Western blotting, competitive immunoprecipitation assays, or cross-blocking binding assays can be used to determine if the antibodies are p75 heterodimer specific.

In addition to mice, mammals such as rats and rabbits deficient in the IL-12 p35 subunit gene and/or IL-12 p40 subunit gene, can be immunized with the IL-12 p75 heterodimer to produce the antibodies described herein. The deficiency or mutation in the IL-12 p35 subunit gene and/or IL-12 p40 subunit gene can be any deficiency or mutation that results in lack of expression of IL-12 p75 heterodimer. Furthermore, any conventional method for obtaining mammalian cells carrying a mutation in the IL-12 p35 subunit gene and/or IL-12 p40 subunit gene which results in IL-12 p75 deficient phenotype can be used.

In accordance with the present invention, activated mammalian cells expressing antibodies to the human IL-12 p75 heterodimer can be obtained by immunizing a mouse or other mammal with natural human IL-12 or recombinant IL-12. Natural human IL-12 and recombinant human IL-12 can be prepared by any conventional technique known in the art, such as the techniques provided in the examples herein.

Suitable myeloma cell lines, i.e., fusion partners, for use in producing the hybridomas that secrete the IL-12 antibodies of the present invention include myeloma cell lines well known in the art, such as, for example, SP 2/0 and NS/O cell lines. SP2/0 mouse myeloma cells are preferred. Preferably, the myeloma fusion partner and the mammalian cell activated against the IL-12 p75 heterodimer are derived from the same species.

Hybridoma cells producing the antibodies of the present invention can be selected and isolated by any conventional methods known in the art. Preferably, myeloma cells and lymphocytes activated against the IL-12 p75 heterodimer are cultured together in media containing a selection agent capable of killing the myeloma cells but not the lymphocytes. Hybridomas are formed from myeloma cells that fuse with the lymphocytes activated against the IL-12 p75 heterodimer. Such hybridoma cells are capable of growing in the media containing the selection agent because DNA of the lymphocytes supplies to the myeloma cell line the necessary gene encoding an enzyme that prevents the toxic effects of the selection agent by allowing an alternate metabolic pathway to replace the metabolic pathway blocked by the selection agent. Any unfused lymphocytes die because they are not transformed and have short, finite lifetimes in vitro. In accordance with the present invention a suitable selection agent for use in selecting out hybridoma cells is aminopterin. A preferred medium for cultivating the hybridoma cells is Iscove's Modified Dulbecco's Medium (IMDM) supplemented with 10% FBS (Hyclone), 100 Units/ml penicillin G (BioWhittaker), 100 μg/ml streptomycin (BioWhittaker), 250 ng/ml Fungizone (BioWhittaker), 2 mM glutamine (BioWhittaker), 100 μg/ml gentamicin sulfate (BioWhittaker), 50 μM 2-mercaptoethanol (BioRad), 100 μM hypoxanthine (Sigma), 400 nM aminopterin (Sigma), 16 μM thymidine (Sigma), and 2.5% P388D1 supernatant (produced as described by Nordan, R. P., et al., J. Immunol., 139:813 (1987)).

The potency of the IL-12 antibodies of the present invention is determined with respect to the concentration of IL-12 antibodies at which 50% of maximal inhibition of IL-12 bioactivity occurs as measured by IL-12-stimulated human lymphoblast proliferation or IFN-γ production assays. The anti-human IL-12 antibodies of the present invention exhibit higher potency than previously characterized heterodimer specific IL-12 antibodies. In addition, the anti-human antibodies of the present invention exhibit greater efficacy, as measured by the extent of maximal inhibition of IL-12-stimulated lymphocyte proliferation or IFN-γ production, than previously characterized heterodimer specific IL-12 antibodies.

The potency and efficacy of the antibodies described herein can be determined by any conventional assay known in the art, such as, for example, IL-12 induced lymphoblast proliferation assays or IFN-γ synthesis assays.

In accordance with the present invention, any conventional method known in the art can be used to determine inhibition of human IL-12 stimulated lymphoblast proliferation by the IL-12 antibodies. In general, human lymphocytes can be activated by a number of methods, including treatment with mitogenic lectins, e.g. phytohemagglutinin A (PHA), or other activating agents, alone or in combination, such as cytokines, phobol esters and ionophores, antibodies directed against cell surface molecules, or any other method which will lead to activation of the lymphocytes. The activated lymphocytes are then incubated with and without IL-12 in the absence or presence of the antibodies, and the rate of lymphocyte proliferation is measured by determining the rate of DNA synthesis by measuring the incorporation of $^3$H-thymidine into DNA, by counting the number of cells present after various periods of treatment, or any other method that can be used to monitor the rate of cellular proliferation. Inhibition of proliferation is determined by comparing lymphocyte proliferation at a defined concentration of IL-12 in the absence and presence of various concentrations of anti-IL-12 antibodies.

In a standard lymphocyte proliferation assay, inhibition of human IL-12 stimulated PHA-activated human lymphoblast proliferation is determined with respect to levels of human IL-12 stimulated PHA-activated human lymphoblast proliferation without any added antibodies and background levels of PHA-activated human lymphoblast proliferation, i.e., proliferation in the absence of both IL-12 and antibodies. In general, IL-12-stimulated levels of proliferation yield about 10,000–80,000 cpm in our standard human lymphocyte proliferation assay, with background levels of proliferation yielding about 5,000–20,000 cpm. Due to the inherent variability between batches of stimulated PHA-activated human lymphoblasts, only assays in which the ratio of stimulated proliferation to background proliferation (i.e. the stimulation index) was equal to or greater than 3 are considered valid for the measurement of IL-12-stimulated proliferation.

In accordance with the present invention, any conventional method for determining inhibition of IFN-γ production by the IL-12 antibodies can be used. For example, activated human lymphocytes, prepared as described herein, or activated human peripheral blood mononuclear cells (PBMC), prepared by treating whole blood or isolated PBMC with mitogenic agents including lectins, cytokines, phobol esters, ionophores, or antibodies directed against cell surface molecules, alone or in combination, or by any other method which will lead to the production of activated human PBMC, are incubated with or without IL-12 and various other agents, e.g. IL-2 and/or IL-1β, in the absence and presence of the antibodies. IFN-γ production is then determined, e.g. by sampling the culture medium and determining the concentration of IFN-γ by ELISA or any other method that can quantitatively measure IFN-γ. Inhibition of IFN-γ production is determined by comparing IFN-γ production at a defined concentration of IL-12 in the absence and presence of various concentrations of anti-IL-12 antibodies.

In a standard IFN-γ synthesis assay inhibition of IFN-γ is determined with respect to IL-12-stimulated IFN-γ production and background levels of IFN-γ production, i.e., IFN-γ synthesis in the presence or absence of IL-12. In general, IL-12-stimulated levels of IFN-γ production are about 7–220 ng/ml, with background levels of production yielding about 1–3 ng/ml.

The antibodies herein neutralize rhesus monkey IL-12 bioactivity with a potency similar to their potency for inhibiting human IL-12 bioactivity, making them useful IL-12 antagonists for in vivo studies in the rhesus monkey. The increased potency and efficacy of these anti-human IL-12 antibodies and their cross reactivity with rhesus monkey IL-12 make them excellent candidates for designing effective IL-12 antagonists for use in humans.

In particular, the present invention provides four antibodies, 5F2, 16F2, 16G2 and 20E11 to the p75 heterodimer of human IL-12 which are produced by hybridomas having ATCC designation numbers HB-12446, HB-12447, HB-12449, and HB-12448, respectively. These hybridomas were deposited on Dec. 11, 1997, with the ATCC (American Type Culture Collection), 10801 University Boulevard, Manassas, Va. 20110-2209, under the provisions of the Budapest Treaty on the International Recognition of the Deposit of Microorganisms for the Purposes of Patent Procedure, and comply with the criteria set forth in 37 C.F.R. § 1.801–1.809 regarding availability and permanency of deposits. However, the present invention is not limited to these four antibodies. Any antibodies having the characteristics described herein are encompassed within the present invention.

FIG. 6 provides the nucleotide sequence encoding a portion of the heavy chain variable region of the p75 heterodimer specific 16G2 antibody and the amino acid sequence deduced from this nucleotide sequence. The nucleotide sequence encoding a portion of the heavy chain variable region of the p75 heterodimer specific 20E11 antibody and the amino acid sequence deduced from this nucleotide sequence is provided in FIG. 7. It will be understood by those skilled in the art that conservative amino acid changes can be made in the constant regions of the heterodimer specific IL-12 antibodies herein without significantly affecting the antigen binding specificity/affinity. Heterodimer specific IL-12 antibodies containing amino acid changes in the variable framework regions or complementary determining regions can be expected to have a greater effect on antigen binding specificity/affinity.

The IL-12 antibodies of the present invention can be complete antibodies including two full length heavy chains and two full length light chains. Alternatively, the IL-12 antibodies can be constructs such as single chain antibodies or "mini" antibodies that retain binding activity to one or more epitopes of the IL-12 p75 heterodimer. Such constructs can be prepared by methods known in the art such as, for example, the PCR mediated cloning and assembly of single chain antibodies for expression in *E. coli* (as described in Antibody Engineering, The practical approach series, J. McCafferty, H. R. Hoogenboom, and D. J. Chiswell, editors, Oxford University Press, 1996). In this type of construct, the variable portions of the heavy and light chains of an antibody molecule are PCR amplified from cDNA. The resulting amplicons are then assembled, e.g. in a second PCR step, through a linker DNA that encodes a flexible protein linker composed of the amino acids GLY and SER. This linker allows the variable heavy and light chain portions to fold in such a way that the antigen binding pocket is regenerated and antigen is bound with affinities often comparable to the parent full-length dimeric immunoglobulin molecule.

The IL-12 antibodies of the present invention are useful antagonists for controlling diseases with pathologies that are mediated through immune mechanisms, particularly, diseases associated with increased IL-12 bioactivity that results in aberrant Thl-type helper cell activity. In accordance with the present invention, the IL-12 antibodies are used for treating autoimmune disorders in humans or other mammals, such as, for example, multiple sclerosis, rheumatoid arthritis, autoimmune diabetes mellitus, and inflammatory bowel disease (IBD) including Crohn's disease and ulcerative colitis. The antibodies described herein can also be used to treat other disease conditions which have been shown to benefit from the administration of IL-12 antibodies including, for example, transplantation/graft-versus-host disease and septic shock.

The dose ranges for the administration of the IL-12 antibodies herein may be determined by those of ordinary skill in the art without undue experimentation. In general, appropriate dosages are those which are large enough to produce the desired effect, i.e., neutralizing at least 90% IL-12 bioactivity. However, the dosage should not be so large as to cause adverse side effects, such as unwanted cross-reactions, anaphylactic reactions, and the like. Generally, the dosage will vary with the age, condition, sex and extent of disease in the patient, counter indications, if any, immune tolerance and other such variables, to be adjusted by the individual physician.

The IL-12 antibodies may be administered parenterally by injection or by gradual perfusion over time. They can be administered intravenously, intramuscularly, or subcutaneously. Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, *Remington's Pharmaceutical Science*, 16th Ed., Mack Eds., 1980, which is incorporated herein by reference.

Preferred dosages of the IL-12 antibodies of the present invention are from about 0.1 mg/kg to about 10 mg/kg, two to three times per week. However, the dosage and dosage schedule for administration of the IL-12 antibodies herein may vary depending on the individual to be treated, the antibody administered, and the variables discussed above. In accordance with the present invention, the IL-12 antibodies may be administered alone or in combination with other therapeutically active agents.

The anti-human IL-12 antibodies described herein may be humanized to form antibodies that possess the same or substantially similar affinity for the IL-12 p75 heterodimer as mammalian anti-human IL-12 antibodies, but are substantially non-immunogenic in humans. For example, a humanized IL-12 antibody in accordance with the present invention can include heavy and light chain framework regions of human antibodies. Preferably, the amino acid sequences of the humanized antibody framework regions are from about 60% to 95% identical to the donor framework regions. The humanized antibodies may be produced by recombinant techniques well known in the art. Methods for producing humanized immunoglobulins are described in U.S. Pat. No. 5,530,101, the disclosure of which is incorporated herein by reference.

The following examples set forth herein below are provided so that the invention herein described may be more fully understood. These examples are provided for illustrative purposes only and should not be construed as limiting this invention in any way to the specific embodiments recited therein.

EXAMPLE 1

Preparation of Natural Human IL-12

Blood was drawn from normal volunteer donors into syringes containing preservative-free heparin (Sigma, St. Louis, Mo.) to give a final concentration of ~5 units heparin/ml blood. One volume of heparinized blood was diluted into 9 volumes of medium consisting of a 1:1 mixture of RPMI 1640 and Dulbecco's modified Eagle's medium, supplemented with 0.1 mM nonessential amino acids, 60 $\mu$g/ml arginine HCl, 10 mM HEPES buffer, 2 mM L-glutamine, 100 U/ml penicillin, 100 $\mu$g/ml streptomycin (all available from GIBCO BRL, Grand Island, N.Y.), 50 $\mu$M 2-mercaptoethanol (Fisher Scientific, Fair Lawn, N.J.), and 1 mg/ml dextrose (Fisher). To this mixture was added human interferon-$\gamma$, 20 U/ml, (PeproTech, Inc., Rocky Hill, N.J.) and Pansorbin cells (formalinized *Staphylococcus aureus*, Cowan strain; Calbiochem, San Diego, Calif.) at a final dilution of 1/4000. (Prior to use in the cultures, Pansorbin cells were washed 2 times with Dulbecco's phosphate-buffered saline (GIBCO BRL) and reconstituted to the same volume as supplied by the manufacturer.) The resulting cell suspension was aliquoted into 162 $cm^2$ tissue culture flasks (Costar, Cambridge, Mass.), 80 ml/flask, and the flasks were incubated horizontally at 37° C. in a humidified atmosphere of 5% $CO_2$/95% air for 24 hours. The culture supernatant fluids were then harvested by centrifugation and sterilized by filtration through a 0.22 $\mu$m filter (Costar). IL-12 heterodimer plus IL-12 p40 were purified from the culture supernatants by immunoaffinity chromatography using a 2-4A1 protein G sepharose (PGS) column, as described below for the purification of rhesus IL-12, except that the elution buffer contained 0.01% gelatin (Sigma) to minimize protein loss due to nonspecific adsorption to surfaces. The eluate was dialyzed for 4 to 6 hours against 100–200 volumes of Dulbecco's phosphate-buffered saline, and then overnight against the same volume of RPMI 1640 containing 100 $\mu$g/ml gentamicin. The dialyzed eluates were sterilized by passage through a 0.22 $\mu$m filter, and then assayed by ELISA for content of IL-12 heterodimer and IL-12 p40 (Gately, M. K., Chizzonite, R. and Presky, D. H., Measurement of human and mouse interleukin 12, *Current Protocols in Immunology*, vol. 1. J. E. Coligan, A. M. Kruisbeek, D. H. Margulies, E. M. Shevach, and W. Strober, eds., John Wiley & Sons, Inc., New York, 1995, pp. 6.16.1–6.16.15) and for IL-12 bioactivity (ibid.). Typically, the weight ratio of IL-12 p40:IL-12 heterodimer, as measured by ELISA, was approximately 5:1.

EXAMPLE 2

Production of Recombinant Human IL-12

Recombinant Human IL-12 was prepared, characterized, and generated as set forth in U.S. Pat. No. 5,536,657 the contents of which are expressly incorporated herein by reference.

EXAMPLE 3

Generation of Rhesus Monkey IL-12

The p35 and p40 subunit cDNA sequences for rhesus monkey IL-12 (F. Villinger et al., J. Immunol., 155:3946–3954 (1995)) were engineered for expression in CHO-dhfr minus cells on two separate plasmids using standard procedures (Current protocols in molecular biology, F. Ausubel, ed., J. Wiley and Sons, Inc., New York (1993)). Clones were obtained from an unamplified cell population and their IL-12 production was monitored by an IL-12 specific ELISA. An optimally producing clone was selected and adapted to growth in CHO serum-free medium (Sigma). The cells were subsequently grown in spinner cultures for protein production purposes. Rhesus monkey IL-12 was purified from the supernatants by antibody affinity chromatography. The affinity column was produced by crosslinking 10 mg of anti-human IL-12 p40 mAb 2-4A1 (Chizzonite et al., J. Immunol., 147:1548–1556 (1991)) to Protein G Sepharose (Pharmacia Biotech) using 10 mM dimethyl pimelimidate (Pierce, Rockford, Ill.) at a density of 1 mg mAb/ml of gel (Stem and Podlaski, Tech. In Protein Chem. IV, Acad. Press, New York, 353–360 (1993)). The serum-free CHO supernatant containing rhesus IL-12 was filtered through a 0.2 $\mu$m filter and loaded directly onto the 10 ml 2-4A1 PGS column previously equilibrated in PBS pH 7.2. The flow rate was 1 ml/min. The column was washed with 10 volumes of PBS and eluted with 0.1M Glycine-HCL, 0.15M NaCl pH 3.0. The eluate was immediately neutralized with 3M Tris-HCl, pH 9. The affinity column was able to bind ~2 mgs of rhesus IL-12/run, including excess p40 monomer, as determined by Bradford and SDS-PAGE. Other contaminants were at trace levels. To concentrate and further purify the rhesus IL-12, the IL-12-containing eluate was dialzyed against 20 mM Na Phosphate, pH 7, and loaded onto a S-Sepharose column conditioned with the same buffer solution. The flow rate was 1 ml/min. All protein was bound. The column was washed with 10 volumes of phosphate buffer and then eluted with phosphate buffer containing 0.3M NaCl. The eluted pool was assayed for endotoxin using the LAL kit from Biowittaker and found to be <10 EU/mg of protein. Western Blot analysis using the mAb 2-4A1 as detection reagent showed the rhesus IL-12 heterodimer at ~80 kDa as well as an apparent excess of p40 monomer at 40 kDa. Coomassie stained SDS-PAGE shows an additional prominent protein of equal intensity to the p80 heterodimer at ~70 kDa. Both the 80 and 70 kDa proteins are reduced to their monomeric forms after treatment with 2-mercaptoethanol but the latter protein band does not react with mAb 2-4A1.

EXAMPLE 4

Preparation, Characterization, and Purification of Hybridoma Antibodies

Mice carrying a mutation in the IL-12 p35 subunit gene on the Balb/c background were produced as described in Mattner, F., et al., Eur. J. Immunol., 26:1553–1559 (1996). The IL-12 p35-deficient mice were immunized intraperitonealy with 5 $\mu$g of purified recombinant human IL-12 in complete Freund's adjuvant. The mice received 3 subsequent intraperitoneal booster injections of 5 $\mu$g human IL-12 in incomplete Freund's adjuvant over a 2.5 month period. Final injections of 75 $\mu$g human IL-12 in PBS (50 $\mu$g i.p. and 25 $\mu$g i.v.) were given three and two days before splenectomy, followed by an i.p. injection of 50 $\mu$g of human IL-12 in PBS one day before splenectomy. Splenocytes were harvested from these mice and fused to mouse myeloma SP2/0 cells at a ratio of 1:1 using 50% w/v polyethylene glycol 1500 (Boehringer Mannheim) according to the method of Oi and Herzenberg, in Selected Methods in Cellular Immunology, ed. B. Mishell and S. Shiigi, W. H. Freeman and Co., New York, 1980, pp.351–372. The fused cells were plated at a density of 60,000 total cells/well in 96-well cluster plates in IMDM supplemented with 10% FBS (Hyclone), 100 Units/ml penicillin G (BioWhittaker), 100 $\mu$g/ml streptomycin (BioWhittaker), 250 ng/ml Fungizone (BioWhittaker), 2 mM glutamine (BioWhittaker), 100 $\mu$g/ml gentamicin sulfate (BioWhittaker), 50 $\mu$M 2-mercaptoethanol (BioRad), 100 $\mu$M hypoxanthine (Sigma), 400 nM aminopterin (Sigma), 16 $\mu$M thymidine (Sigma), and 2.5% P388D1 supernatant (produced as described by Nordan, R. P., et al., J. Immunol., 139:813 (1987)). Hybridoma supernatants were assayed for specific anti-human IL-12 antibodies by immunoprecipitation of $^{125}$I-labeled human IL-12 as described below. Hybridoma cell lines secreting anti-human IL-12 antibodies were cloned by limiting dilution. Antibodies were purified from ascites by sequential treatment with caprylic acid and ammonium sulfate as previously described (Reik, L. et al., J. Immunol. Methods, 100:123–130 (1987).

EXAMPLE 5

Preparation of $^{125}$I-labeled Human IL-12

Recombinant human IL-12 was radiolabeled to a specific activity of about 2200 Ci/mmol using a modification of the Iodogen (Pierce Chemical Co.) procedure previously described in Chizzonite et al., J. Immunol., 147: 1548–1556 (1991) and Chizzonite et al., J. Immunol., 148: 3117–3124 (1992) which are incorporated herein by reference. Iodogen was dissolved in chloroform and 0.05 mg dried in a 12×15 mm borosilicate glass tube. For radiolabeling, 1.0 mCi Na[$^{125}$I] (Amersham, Chicago, Ill.) was added to an Iodogen-coated tube containing 0.05 ml of Tris-iodination buffer (25 mM Tris-HCL pH 7.5, 0.4 M NaCl and 1 mM EDTA) and incubated for 6 min at room temperature. The activated $^{125}$I solution was transferred to a tube containing 0.1 ml IL-12 (31.5 $\mu$g) in Tris-iodination buffer and the reaction was incubated for 6 minutes at room temperature. At the end of the incubation, 0.05 ml of Iodogen stop buffer (10 mg/ml tyrosine, 10% glycerol in Dulbecco's PBS, pH 7.40) was added and reacted for 5 minutes. The mixture was then diluted with 1% (w/v) BSA in 1.0 ml Tris-iodination buffer, and applied to a Bio-Gel P10DG desalting column (BioRad Laboratories (BRL)) for chromatography. The column was eluted with 1% (w/v) BSA in Tris-iodination buffer, and fractions (1 ml) containing the peak amounts of labeled protein were combined and diluted to 1×10$^8$ cpm/ml with 1% (w/v) BSA in Tris-iodination buffer. The TCA preciptable radioactivity (10% TCA final concentration) was typically in excess of 95% of the total radioactivity. The radiospecific activity of the recombinant human IL-12 was typically about 2200 Ci/mmol.

EXAMPLE 6

Immunoprecipitation Assay of $^{125}$I-labeled Human IL-12

Nunc Maxisorp 96-well break-apart plates were coated with rabbit affinity purified antibody to mouse IgG (Cappel, Durham, N.C.) by incubating 18 hrs at 4° C. with 100 $\mu$l/well of 5 $\mu$g/ml rabbit anti-mouse IgG in carbonate coating buffer (15 mM Na$_2$CO$_3$/35 mM NaHCO$_3$), pH 9.6. The coated wells were washed with PBS/0.05% Tween-20/0.01% Thimerosol and then blocked by incubation with 200 µl of 1% (w/v) BSA/PBS/0.01% Thimerosol for 4 hrs at 37° C. Hybridoma supernatants (75 µl) were added to the anti-mouse IgG-coated wells and incubated for 3 hrs at 22° C. The wells were washed 3 times with 300 µl of PBS/0.05% Tween-20/0.01% Thimerosol, and then 100,000 cpm of $^{125}$I-labeled human IL-12 were added to each well in 100 µl of antibody diluting buffer (PBS/1% BSA (w/v)/0.5 M NaCl/0.05% Tween-20/0.01% Thimerosol). After 18 hrs at 4° C., the wells were washed 3 times with 200 µl of PBS/0.05% Tween-20/0.01% Thimerosol. The wells were then separated and the amount of radioactivity bound to the wells was determined using a gamma counter. In some experiments, following the incubation of the hybridoma supernatants in the rabbit anti-mouse IgG-coated wells, 100 µl of conditioned supernatant from human IL-12 p40-transfected COS cells prepared as previously described (Gubler et al., Proc. Natl. Acad. Sci. 88: 4143–4147 (1991)) were incubated in the wells for 1 hr at 37° C. prior to addition of $^{125}$I-labeled human IL-12 to determine if the captured mouse anti-human IL-12 antibodies bound to the p40 subunit of human IL-12.

EXAMPLE 7

Identification of Monoclonal Anti-Human IL-12 Antibodies

A 96-well plate-based immunoprecipitation assay was used to identify hybridomas secreting anti-human IL-12 antibodies. Hybridoma supernatants were incubated in the absence and presence of 100 µl COS cell supernatant containing human IL-12 p40 subunit as described above. $^{125}$I-labeled human IL-12 (100,000 cpm/well) was added, and the amount of $^{125}$I-labeled human IL-12 captured onto the wells was determined. FIG. 1 shows that antibodies contained in supernatants from hybridomas 5F2, 16F2, 16G2, 20E11 and 17E2 captured $^{125}$I-labeled human IL-12. In addition, the presence of unlabeled human IL-12 p40 subunit during the immunoprecipitation reaction did not block capture of $^{125}$I-labeled human IL-12 by the antibodies 5F2, 16F2, 16G2 and 20E11, demonstrating that these antibodies do not have high affinity for the IL-12 p40 subunit alone. In contrast, the presence of unlabeled human IL-12 p40 subunit during the immunoprecipitation reaction completely blocked capture of $^{125}$I-labeled human IL-12 by 17E2, demonstrating that 17E2 recognized the p40 subunit of human IL-12.

EXAMPLE 8

Analytical Isoelectric Focusing of Anti-Human IL-12 Monoclonal Antibodies

Figure 2:
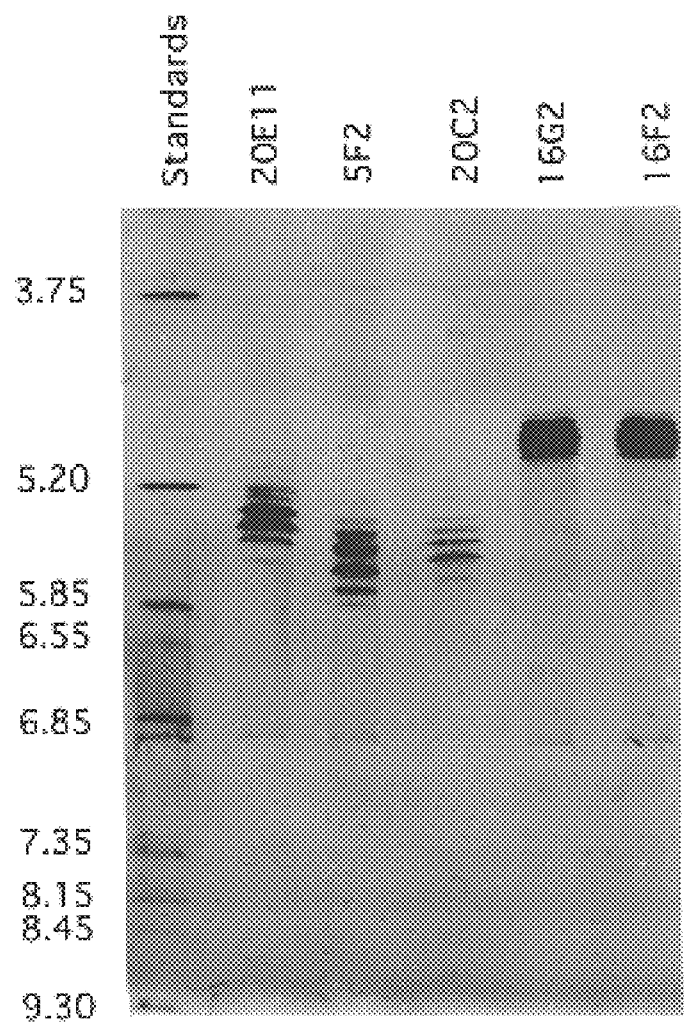
FIG. 2 shows isoelectric focusing patterns of p75 heterodimer specific anti-human IL-12 monoclonal antibodies 20C2, 16G2, 16F2, 20E11, and 5F2.

Analytical isoelectric focusing was performed using a pH 3.5–9.5 Ampholine PAGplate from Pharmacia Biotech (code no. 80-1124-80, Uppsala, Sweden). Isoelectric focusing was done according to the manufacturer's instructions using electrode solutions of 1 M phosphoric acid and 1N sodium hydroxide. The gel was loaded with 5 samples, each of which contained a single immunoglobulin, i.e., 20E11, 5F2, 20C2, 16G2 and 16F2. Standards were from the Isoelectric Focusing pH 3–10 Calibration Kit from Pharmacia Biotech (code no. 17-0471 -01). Running conditions were 1000 volts, 10 watts, 2.5 hours, 4° C. The gel was silver stained using the Pharmacia Biotech PlusOne Silver Staining Kit for protein (code no. 17-1150-01) according to the manufacturer's directions. FIG. 2 shows the isoelectric focusing patterns of anti-human IL-12 monoclonal antibodies 20C2, 16G2, 16F2, 20E11, and 5F2.

EXAMPLE 9

Isoelectric Focusing Patterns of the Anti-Human IL-12 Monoclonal Antibodies

As shown in FIG. 2, monoclonal antibodies 20C2 (Chizzonite et al., Cytokine, 6: A82a (1994)), 20E11, and 5F2 are unique immunoglobulins. Monoclonal antibodies 16G2 and 16F2 appear identical by isoelectric focusing, but both are different from 20C2, 20E11 and 5F2. The pI of these antibodies is in the range of pH 5–6.

EXAMPLE 10

Generation of PHA-Activated Lymphoblasts

Day 4 PHA-activated human peripheral blood mononuclear cells (PBMC) were used in determining both natural human IL-12-induced and rhesus monkey IL-12-induced proliferation. PBMC were isolated (Gately et al., J. Natl. Cancer Inst., 69:1245 (1982)) and stimulated with 0.1% PHA-P (Difco Labs., Detroit, Mich.). After 3 days, the cultures were split 1:1 with fresh medium and recombinant 50 U/ml human IL-2 (provided by Dr. F. Khan, Hoffmann-La Roche Inc.) as described (Gately, M. K., Chizzonite, R. and Presky, D. H., Measurement of human and mouse interleukin 12, *Current Protocols in Immunology*, vol. 1., J. E. Coligan, A. M. Kruisbeek, D. H. Margulies, E. M. Shevach, and W. Strober, eds., John Wiley & Sons, Inc., New York, 1995, pp. 6.16.1–6.16.15). Supplemented medium used for cell culture was as described previously for the production of natural human IL-12 with the addition of 5% human AB serum (Irvine Scientific, Santa Ana, Calif.).

EXAMPLE 11

Lymphocyte Proliferation Assay

The effects of the various anti-human IL-12 monoclonal antibodies on IL-12- and IL-2-stimulated PHA-activated human lymphoblast proliferation was determined by a method based on M. K. Gately et al. (Gately, M. K., Chizzonite, R. and Presky, D. H., Measurement of human and mouse interleukin 12, *Current Protocols in Immunology*, vol. 1., J. E. Coligan, A. M. Kruisbeek, D. H. Margulies, E. M. Shevach, and W. Strober, eds., John Wiley & Sons, Inc., New York, 1995, pp. 6.16.1–6.16.15). Day 4 PHA-activated lymphoblasts, prepared as described above, were harvested, washed and resuspended in supplemented medium at $4\times10^5$ cells/ml and incubated in 96-well plates ($2\times10^4$ cells/well) with purified monoclonal anti-human IL-12 antibody and the relevant cytokine, i.e. human or monkey IL-12. Twenty five µl aliquots of both natural human IL-12 at 1 ng/ml or monkey IL-12 at 2 ng/ml were mixed with 25 µl aliquots of various dilutions of anti-human IL-12 monoclonal antibodies (mAbs). The final antibody concentration in the wells varied from 0.0005 µg/ml up to 0.5 µg/ml. A separate, identical set of wells containing the various anti-human IL-12 mAbs and recombinant IL-2 was prepared to determine the effects of the anti-human IL-12 mAbs on IL-2-stimulated proliferation as a measure of inhibitory specificity. A standard dose-response curve ranging from 250 pg or 500 pg per well human or monkey IL-12, respectively, down to 0 pg without added antibodies was also included to determine IL-12-responsiveness. Plates containing mixtures of cytokines and antibodies were incubated for 30 minutes at 37° C., and then 50 μl aliquots of cell suspension were added to the wells. The culture plates were maintained at 37° C. in a humidified atmosphere of 5% $CO_2$ in air for 48 hours prior to $^3$H-thymidine pulsing. Fifty μl of 10 μCi/ml $^3$H-thymidine (diluted in supplemented media with 5% FCS in lieu of 5% human AB serum) were added to each well. After incubation for an additional 6 hr at 37° C., the well contents were harvested onto glass fiber filters via a cell harvester, and $^3$H-thymidine incorporation into cellular DNA was measured by use of a liquid scintillation counter. Values shown in FIGS. 3 and 4 are the means of triplicate wells.

EXAMPLE 12

Figure 3:
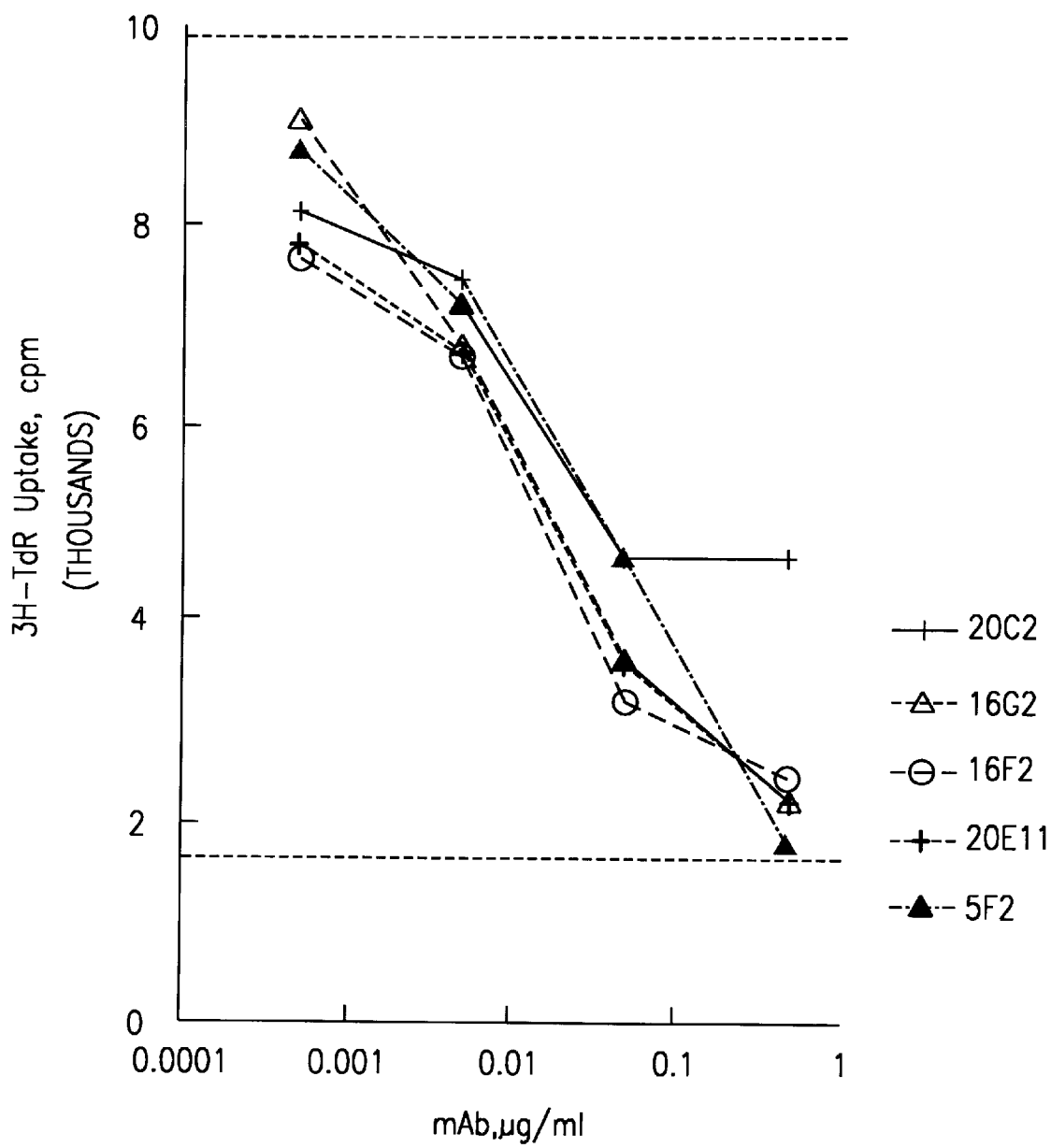
FIG. 3 is a plot showing inhibition of natural human IL-12 stimulated PHA-activated human lymphoblast proliferation by p75 heterodimer specific IL-12 monoclonal antibodies 20C2 (+), 16G2 (Δ), 16F2 (○), 20E11 (:), and 5F2 (s). Inhibition of natural human IL-12 stimulated PHA-activated human lymphoblast proliferation was determined with respect to the level of 0.25 ng/ml human IL-12 stimulated PHA-activated human lymphoblast proliferation in the absence of IL-12 antibodies, shown in FIG. 3 as a horizontal dotted line at 9940 cpm, and background levels of PHA-activated human lymphoblast proliferation, i.e., in the absence of both IL-12 and IL-12 antibodies, shown in FIG. 3 as a horizontal dotted line at 1480 cpm.
Figure 4:
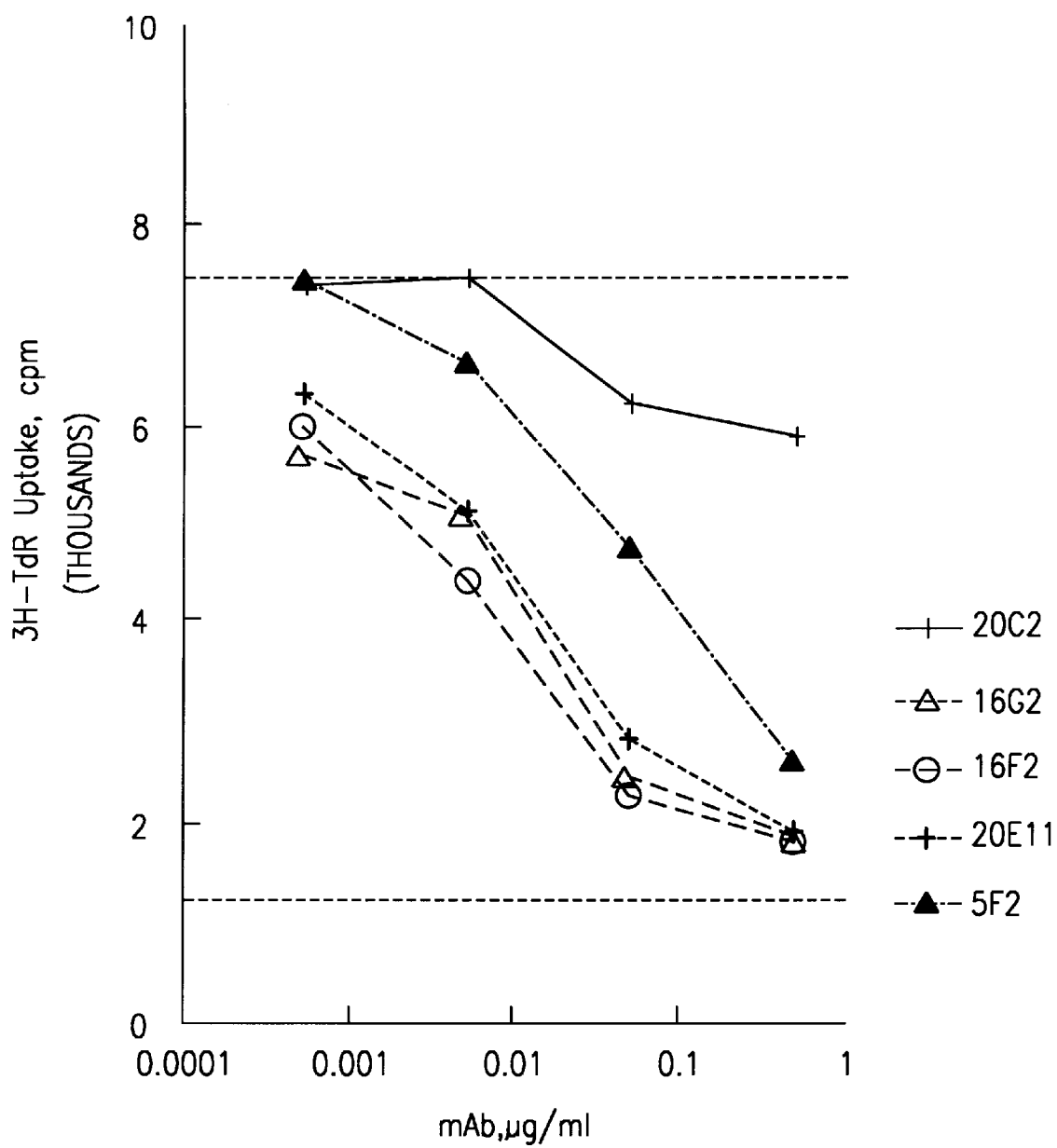
FIG. 4 is a plot showing inhibition of rhesus monkey IL-12 stimulated PHA-activated human lymphoblast proliferation by p75 heterodimer specific IL-12 monoclonal antibodies 16G2 (Δ), 16F2 (○), 20E11 (:) and 5F2 (s) of the present invention compared to the previously known 20C2 (+) antibody. The level of lymphoblast proliferation in the presence of 0.5 ng/ml rhesus monkey IL-12 and in the absence of IL-12 antibodies is represented by the horizontal dotted line at the upper end of the plot. The background level of lymphoblast proliferation, i.e., in the absence of both IL-12 and IL-12 antibodies is represented by a horizontal dotted line at the lower end of the plot.

Inhibition of Cytokine-Stimulated PHA-Activated Lymphoblast Proliferation by Monoclonal Anti-Human IL-12 Antibodies Proliferation of PHA-activated human lymphoblasts stimulated with 0.25 ng/ml IL-12 was inhibited in a dose-dependent fashion by antibodies 5F2, 16F2, 16G2, and 20E11 (FIG. 3). The potencies of these anti-human antibodies, defined as the concentration that produces 50% of maximal inhibition ($IC_{50}$) of 0.25 ng/ml IL-12-stimulated proliferation, are 0.03 μg/ml for 5F2, 0.01 μg/ml for 16F2, 0.01 μg/ml for 16G2, and 0.01 μg/ml for 20E11. The maximal (9440 cpm) and background (1480 cpm) levels of lymphoblast proliferation are represented by the horizontal dotted lines at the upper and lower ends of the plots, respectively. As shown in FIG. 3, the 5F2, 16F2, 16G2, and 20E11 antibodies were able to inhibit human IL-12 stimulated PHA activated lymphoblast proliferation by at least 90%. In contrast, as also shown in FIG. 3, the previously identified anti-human IL-12 p75-specific antibody 20C2 (Chizzonite et al., Cytokine, 6: A82a (1994)) is not able to substantially inhibit human IL-12 bioactivity.

In addition, as shown in FIG. 4, 5F2, 16F2, 16G2, and 20E11 potently inhibited proliferation of PHA-activated human lymphoblasts stimulated with 0.5 ng/ml rhesus monkey IL-12, with a similar $IC_{50}$ to that seen with human IL-12-stimulated proliferation. In contrast, 20C2 has only a minimal inhibitory effect on rhesus monkey IL-12-stimulated proliferation. Therefore, the antibodies 5F2, 16F2, 16G2, and 20E11 appear to exhibit good cross-reactivity to rhesus monkey IL-12, whereas the cross-reactivity of 20C2 is much less. None of these monoclonal antibodies inhibited IL-2-induced proliferation, demonstrating that their effect on IL-12-stimulated proliferation was specific for IL-12 and was not due to a general inhibition of cell proliferation.

EXAMPLE 13

Interferon-γ Synthesis Assay

Interferon-γ (IFN-γ) synthesis was induced using Day 4 PHA-activated human lymphoblasts produced as described above. The medium used was a 1:1 mixture of RPMI 1640 and Dulbecco's modified Eagle's medium supplemented as described above for preparation of natural human IL-12 and containing, in addition, 5% heat-inactivated (56° C., 30 min) fetal bovine serum (Hyclone, Logan, Utah) in lieu of human AB serum. Duplicate 1 ml cultures were set up in the wells of 24-well tissue culture plates (Costar). To each well was added 5×10$^5$ PHA-activated lymphoblasts, 0.25 ng/ml purified natural human IL-12, 20 units/ml recombinant human IL-2, 1 ng/ml recombinant human IL-1β (provided by Dr. R. Chizzonite, Hoffmann-La Roche), and the indicated concentrations of anti-human IL-12 antibodies. Initially, all reagents except the lymphoblasts were added to the wells and incubated at 37° C. for 30 min, followed by the addition of the lymphoblasts. The cultures were then incubated for 24 hr at 37° C. in a humidified atmosphere of 5% $CO_2$ in air. At the end of this time, the culture supernatant fluids were harvested by centrifugation and assayed for their content of IFN-γ by use of an ELISA. The amount of IFN-γ produced in cultures containing lymphoblasts with IL-2+IL-1 but no IL-12 was always less than 15% and usually less than 5% of that produced in cultures containing 0.25 ng/ml IL-12 in addition to IL-2+IL-1.

The ELISA for measuring human IFN-γ used monoclonal anti-human IFN-γ antibodies from Endogen (Woburn, Mass.). Nunc EIA plates (Fisher) were coated overnight at 4° C. with 100 μl/well of 1 μg/ml anti-human IFN-γ (Endogen #M-700A) in coating buffer (0.015 M $Na_2CO_3$+ 0.035 M $NaHCO_3$ in distilled water, pH 9.6). The following morning, the coating buffer was flicked out of the wells, and the wells were blocked by addition of 200 μl/well of Dulbecco's phosphate-buffered saline (D-PBS; Fisher) containing 1% bovine serum albumin (Sigma). After incubation for 1 hr at room temperature, the plates were washed with D-PBS containing 0.05% tween 20 (Sigma), and 100 μl aliquots of recombinant human IFN-γ standard (Endogen) or culture supernatants diluted in assay buffer (D-PBS+0.5% bovine serum albumin+0.05% tween 20) were added to the wells. The plates were then incubated for 2 hours at room temperature with shaking. Following this, the plates were again washed, and each well received 100 μl of 300 ng/ml biotinylated anti-human IFN-γ (Endogen #M-701-B) in assay buffer. The plates were incubated for 1 hr at 37° C., followed by washing. One hundred μl aliquots of streptavidin-peroxidase (Sigma) diluted 1:1000 in assay buffer were then added to each well, and the plates were incubated for 30 min at 37° C. The plates were again washed and then developed by addition of 100 μl aliquots of a 1:1 mix of TMB Peroxidase Substrate and Peroxidase B Solution (Kirkegaard & Perry Laboratories, Gaithersburg, Md.). The reaction was stopped after ~12 min by addition of 50 μl/well of 1 M $H_3PO_4$, and the absorbance was read at 450 nm with subtraction of background at 650 nm.

EXAMPLE 14

Figure 5:
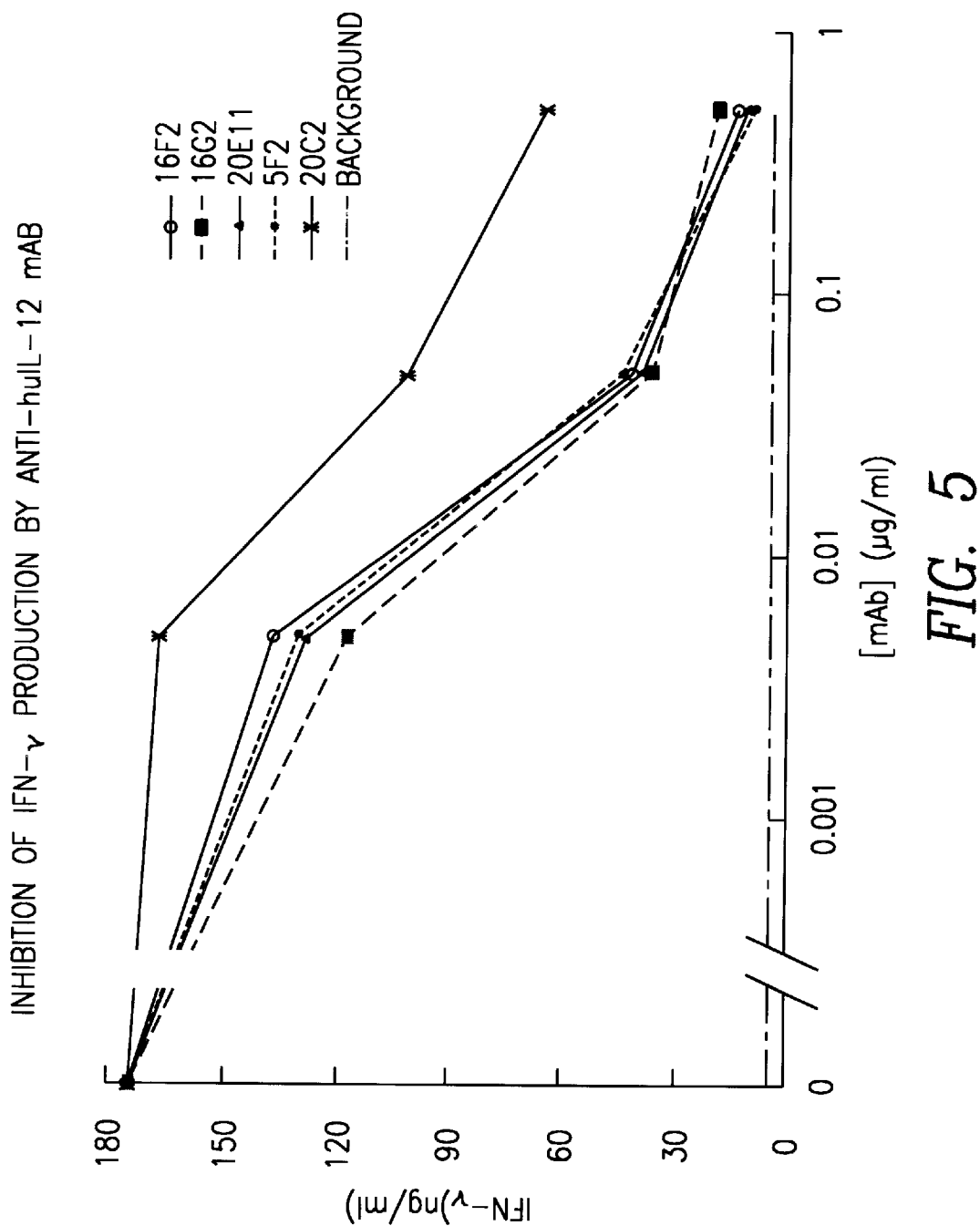
FIG. 5 is a plot showing inhibition of IFN-γ production by p75 heterodimer specific monoclonal antibodies, 16F2 (○), 16G2 (■), 20E11 (s), 5F2 (●) and 20C2 (Q).

Inhibition of Cytokine-Stimulated Interferon-γ Production by Monoclonal Anti-Human IL-12 Antibodies Production of IFN-γ by PHA-activated human lymphoblasts stimulated with 0.25 ng/ml human IL-12 was inhibited in a dose-dependent fashion by antibodies 5F2, 16F2, 16G2, and 20E11 (FIG. 5). The potencies of these anti-human antibodies, defined as the concentration that produces 50% of maximal inhibition ($IC_{50}$) of 0.25 ng/ml human IL-12-stimulated IFN-γ production, are 0.02 μg/ml for 5F2, 0.02 μg/ml for 16F2, 0.01 μg/ml for 16G2, and 0.02 μg/ml for 20E11. These anti-human heterodimer specific IL-12 antibodies were able to inhibit greater than 90% of IL-12-stimulated IFN-γ production when used at 0.5 μg/ml. In contrast, the previously identified anti-human IL-12 p75-specific antibody 20C2 (Chizzonite et al., Cytokine, 6: A82a (1994)) is less potent and is unable to inhibit IL-12-stimulated IFN-γ production by more than 65% at concentrations less than or equal to 0.5 μg/ml.

EXAMPLE 15

Sequence Analysis of the Genes Encoding the Variable Region of the Antibody Heavy Chains Present in the Anti-Human IL-12 Antibody-Producing Hybridoma Cell Lines Total RNA was extracted from hybridoma cells using the Ultraspec RNA isolation system following the manufacturer's protocol (Biotecx, Houston, Tex.). First strand cDNA was synthesized from 10 µg of total RNA and oligo-dT primers in a 20 µl volume. A 4 µl aliquot of the cDNA reaction mix was used as template for the PCR amplification of the mouse IgG heavy chain variable region using primers that were designed according to the sequence information of framework 1 and 4 as reported by Dattamajumdar et al. (A. K. Dattamajumdar et al., Immunogenetics 43:141–151 (1996)). A 30-cycle PCR reaction was performed using an annealing temperature of 50° C. The entire PCR reaction was phenol extracted, ethanol precipitated, and run on a 1% lo-melt agarose gel to isolate the amplicon. The DNA fragment was excised from the gel, melted at 70° C., and 5 µl was reamplified in a 30-cycle PCR reaction to generate more material. The reamplified amplicon was gel purified and sequenced using a flourescence-based Sanger method of sequencing with an Applied Biosystems Incorporated automated sequencer.

EXAMPLE 16

Nucleotide and Deduced Amino Acid Sequences of the Variable Region of the Monoclonal Anti-Human IL-12 Antibody Heavy Chains The nucleotide sequences of a portion of the variable region of the immunoglobulin heavy chain gene encompassing framework region (FR) 1, complementarity determining region (CDR) 1, FR2, CDR2, FR3, CDR3, and FR4 of IL-12 antibodies produced by hybridoma cell lines HIL-12F3-16G2 and HIL-12F3-20E11 and the deduced amino acid sequences thereof are shown in FIG. 6 and FIG. 7, respectively. The CDR sequences are underlined. Comparison of available sequence information showed that the heavy chains of antibodies produced by hybridomas HIL-12F3-16G2 and HIL-12F3-20E11 exhibit 94% homology at the DNA level and 93% similarity at the amino acid level.

What is claimed is:

1. An antibody to the human IL-12 p75 heterodimer, said heterodimer consisting a p35 subunit and a p40 subunit, wherein said antibody
   (a) immunologically reacts with an epitope presented by the p75 heterodimer of human IL-12, but is not immunologically reactive with any epitope presented by said p40 subunit; and
   (b) is produced from a hybridoma cell line obtained from a mouse which is deficient in the gene encoding said p35 subunit or the p40 subunit of IL-12, said hybridoma cell line being selected from the group consisting of ATCC designation HB-12446, HB-12447, HB-12448, and HB-12449, or a humanized antibody, thereof.

2. A monoclonal antibody to human IL-12, said human IL-12 consisting of a p35 subunit and a p40 subunit which form a p75 heterodimer, wherein said monoclonal antibody
   (a) immunologically reacts with an epitope presented by the p75 heterodimer of human IL-12, but is not immunologically reactive with an epitope presented by said p40 subunit;
   (b) neutralizes at least about 90% of the bioactivity of human IL-12; and
   (c) is produced from a hybridoma cell line selected from the group consisting of ATCC designation Nos. HB-12446, HB-12447, HB-12448, and HB-12449, or a humanized antibody, thereof.

3. A hybridoma that is capable of producing a monoclonal antibody to human IL-12, said human IL-12 consisting of a p35 subunit and a p40 subunit which form a p75 heterodimer, wherein said antibody
   (a) immunologically reacts with an epitope presented by the p75 heterodimer of human IL-12, but is not immunologically reactive with any epitope presented by said p40 subunit; and
   (b) is produced from a cell line obtained from a mouse deficient in a gene encoding said p35 subunit or said p40 subunit, said hybridoma cell line being selected from the group consisting of ATCC designation HB-12446, HB-12447, HB-12448, and HB-12449.

4. The antibody of claim 1, wherein the antibody is produced by a hybridoma having ATCC designation number HB-12446, or a humanized antibody, thereof.

5. The antibody of claim 4, wherein the antibody is humanized.

6. The antibody of claim 1, wherein the antibody is produced by a hybridoma having ATCC designation number HB-12447, or a humanized antibody, thereof.

7. The antibody of claim 6, wherein the antibody is humanized.

8. The antibody of claim 1, wherein the antibody is produced by a hybridoma having ATCC designation number HB-12448, or a humanized antibody, thereof.

9. The antibody of claim 8, wherein the antibody is humanized.

10. The antibody of claim 1, wherein the antibody produced by a hybridoma having ATCC designation number HB-12449, or a humanized antibody, thereof.

11. The antibody of claim 10, wherein the antibody is humanized.

12. The antibody of claim 2, wherein the antibody is produced by a hybridoma having ATCC designation number HB-12446, or a humanized antibody, thereof.

13. The antibody of claim 12, wherein the antibody is humanized.

14. The antibody of claim 2, wherein the antibody is produced by a hybridoma having ATCC designation number HB-12447, or a humanized antibody, thereof.

15. The antibody of claim 14, wherein the antibody is humanized.

16. The antibody of claim 2, wherein the antibody is produced by a hybridoma having ATCC designation number HB-12448, or a humanized antibody, thereof.

17. The antibody of claim 16, wherein the antibody is humanized.

18. The antibody of claim 2, wherein the antibody is produced by a hybridoma having ATCC designation number HB-12449, or a humanized antibody, thereof.

19. The antibody of claim 18, wherein the antibody is humanized.

20. The hybridoma of claim 3 wherein the hybridoma is HIL-12F3-5F2 having ATCC designation number HB-12446.

21. The hybridoma of claim 3 wherein the hybridoma is HIL-12F3-16F2 having ATCC designation number HB-12447.

22. The hybridoma of claim 3, wherein the hybridoma is HIL-12F3-20E11 having ATCC designation number HB-12448.

23. The hybridoma of claim 3, wherein the hybridoma is HIL-12F3-16G2 having ATCC designation number HB-12449.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 321 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: mouse
      (G) CELL TYPE: Hybridoma
      (H) CELL LINE: HIL-12F3-16G2

(ix) FEATURE:
      (A) NAME/KEY: CDS
      (B) LOCATION: 1..321

(xi) SEQUENCE DESCRIPTION: SEQ ID NO:1:

```
CTG GAG GAG TCA GGA CCT AGC CTC GTG AAA CCT TCT CAG ACT CTG TCC      48
Leu Glu Glu Ser Gly Pro Ser Leu Val Lys Pro Ser Gln Thr Leu Ser
 1               5                  10                  15

CTC ACC TGT TCT GTC ACT GGC GAC TCC ATC ACC AGT GGT TAC TGG AAC      96
Leu Thr Cys Ser Val Thr Gly Asp Ser Ile Thr Ser Gly Tyr Trp Asn
                20                  25                  30

TGG ATC CGG AAA TTC CCA GGG AAT AAA TTT GAG TAC ATG GGA TTC ATA     144
Trp Ile Arg Lys Phe Pro Gly Asn Lys Phe Glu Tyr Met Gly Phe Ile
            35                  40                  45

AGT TAT AGT GGT AGC ACT TAC AAT AAT CCA TCT CTC AAA AAT CGA GTC     192
Ser Tyr Ser Gly Ser Thr Tyr Asn Asn Pro Ser Leu Lys Asn Arg Val
        50                  55                  60

TCC ATC ACT CGA GAC ACA TCC AAT AAC CAG TAC TAC CTG CAG TTG AGT     240
Ser Ile Thr Arg Asp Thr Ser Asn Asn Gln Tyr Tyr Leu Gln Leu Ser
 65                  70                  75                  80

TCT GTG ACT ACT GAG GAC TCA GCC ACA TAT TAC TGT GCA AGA TCT TCG     288
Ser Val Thr Thr Glu Asp Ser Ala Thr Tyr Tyr Cys Ala Arg Ser Ser
                85                  90                  95
```

```
GAT GCT TTG GAC TAC TGG GGC GCA GGG ACC ACG                      321
Asp Ala Leu Asp Tyr Trp Gly Ala Gly Thr Thr
            100                 105
```

(2) INFORMATION FOR SEQ ID NO:2:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:2:

```
Leu Glu Glu Ser Gly Pro Ser Leu Val Lys Pro Ser Gln Thr Leu Ser
 1               5                  10                  15

Leu Thr Cys Ser Val Thr Gly Asp Ser Ile Thr Ser Gly Tyr Trp Asn
                20                  25                  30

Trp Ile Arg Lys Phe Pro Gly Asn Lys Phe Glu Tyr Met Gly Phe Ile
            35                  40                  45

Ser Tyr Ser Gly Ser Thr Tyr Asn Asn Pro Ser Leu Lys Asn Arg Val
        50                  55                  60

Ser Ile Thr Arg Asp Thr Ser Asn Asn Gln Tyr Tyr Leu Gln Leu Ser
65                  70                  75                  80

Ser Val Thr Thr Glu Asp Ser Ala Thr Tyr Tyr Cys Ala Arg Ser Ser
                85                  90                  95

Asp Ala Leu Asp Tyr Trp Gly Ala Gly Thr Thr
            100                 105
```

(2) INFORMATION FOR SEQ ID NO:3:

(i) SEQUENCE CHARACTERISTICS:
        (A) LENGTH: 308 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: mouse
        (G) CELL TYPE: Hybridoma
        (H) CELL LINE: HIL-12F3-20E11

(ix) FEATURE:
        (A) NAME/KEY: CDS
        (B) LOCATION: 1..306

(xi) SEQUENCE DESCRIPTION: SEQ ID NO:3:

```
GAG GAG TCA GGA CCT AGC CTC GTG AAA CCT TCT CAG ACT CTG TCC CTC    48
Glu Glu Ser Gly Pro Ser Leu Val Lys Pro Ser Gln Thr Leu Ser Leu
 1               5                  10                  15

ACC TGT TCT GTC ACT GGC GAC TCC ATC ACC AGT GGT TAC TGG AAC TGG    96
Thr Cys Ser Val Thr Gly Asp Ser Ile Thr Ser Gly Tyr Trp Asn Trp
                20                  25                  30

ATC CGG AAA TTC CCA GAT AAT ACA CTT GAG TAC ATG GGA TAC ATA AGT   144
Ile Arg Lys Phe Pro Asp Asn Thr Leu Glu Tyr Met Gly Tyr Ile Ser
            35                  40                  45

TAC AGT GGT AGT ACT TAC TAC AAT CCA TCT CTC AGA AGT CGA ATC TCC   192
Tyr Ser Gly Ser Thr Tyr Tyr Asn Pro Ser Leu Arg Ser Arg Ile Ser
        50                  55                  60
```

―continued

```
ATC ACT CGA GAC ACA TCC AAG AAC CAG TAC TCC ATG CAG TTG AAT TCT       240
Ile Thr Arg Asp Thr Ser Lys Asn Gln Tyr Ser Met Gln Leu Asn Ser
65                  70                  75                  80

GTG ACT ACT GAG GAC ACA GCC ACA TAT TAC TGT GCA AGA TCC TCG GAT       288
Val Thr Thr Glu Asp Thr Ala Thr Tyr Tyr Cys Ala Arg Ser Ser Asp
                85                  90                  95

GCT ATG GAC TAC TGG GGC GC                                            308
Ala Met Asp Tyr Trp Gly
                100
```

(2) INFORMATION FOR SEQ ID NO:4:

(i) SEQUENCE CHARACTERISTICS:
      (A) LENGTH: 102 amino acids
      (B) TYPE: amino acid
      (D) TOPOLOGY: linear (ii) MOLECULE TYPE: protein (xi) SEQUENCE DESCRIPTION: SEQ ID NO:4:

```
Glu Glu Ser Gly Pro Ser Leu Val Lys Pro Ser Gln Thr Leu Ser Leu
1               5                   10                  15

Thr Cys Ser Val Thr Gly Asp Ser Ile Thr Ser Gly Tyr Trp Asn Trp
                20                  25                  30

Ile Arg Lys Phe Pro Asp Asn Thr Leu Glu Tyr Met Gly Tyr Ile Ser
            35                  40                  45

Tyr Ser Gly Ser Thr Tyr Tyr Asn Pro Ser Leu Arg Ser Arg Ile Ser
        50                  55                  60

Ile Thr Arg Asp Thr Ser Lys Asn Gln Tyr Ser Met Gln Leu Asn Ser
65                  70                  75                  80

Val Thr Thr Glu Asp Thr Ala Thr Tyr Tyr Cys Ala Arg Ser Ser Asp
                85                  90                  95

Ala Met Asp Tyr Trp Gly
                100
```